US010934168B1

(12) United States Patent
Brady et al.

(10) Patent No.: US 10,934,168 B1
(45) Date of Patent: Mar. 2, 2021

(54) SYNTHETIC, MULTIFACETED HALOGENATED, FUNCTIONALIZED FULLERENES ENGINEERED FOR MICROBICIDAL EFFECTS EMPLOYING CONTROLLED CONTACT FOR SAFE THERAPEUTIC AND ENVIRONMENTAL UTILITY

(71) Applicants: Terry Earl Brady, The Valley (AI); Anthony Lee Dellinger, Brown Summit, NC (US); Arnie Lee Robertson, Jr., Highpoint, NC (US); Rachel Tinker-Kulberg, Hillsborough, NC (US)

(72) Inventors: Terry Earl Brady, The Valley (AI); Anthony Lee Dellinger, Brown Summit, NC (US); Arnie Lee Robertson, Jr., Highpoint, NC (US); Rachel Tinker-Kulberg, Hillsborough, NC (US)

( * ) Notice: Subject to any disclaimer, the term of this patent is extended or adjusted under 35 U.S.C. 154(b) by 0 days.

(21) Appl. No.: 16/946,892

(22) Filed: Jul. 10, 2020

Related U.S. Application Data

(60) Provisional application No. 63/013,125, filed on Apr. 21, 2020.

(51) Int. Cl.
  *C01B 32/156* (2017.01)
  *B82Y 30/00* (2011.01)
  (Continued)

(52) U.S. Cl.
  CPC ............ *C01B 32/156* (2017.08); *A01N 59/00* (2013.01); *A61K 33/44* (2013.01); *A61M 1/3692* (2014.02);
  (Continued)

(58) Field of Classification Search
  None
  See application file for complete search history.

(56) References Cited

U.S. PATENT DOCUMENTS 3,730,701 A 5/1973 Isquith et al.
4,721,511 A 1/1988 Kuptis
(Continued)

FOREIGN PATENT DOCUMENTS

WO WO-2017171066 A1 * 10/2017 ............... C09D 5/14

OTHER PUBLICATIONS

Ulrike Denter, Hans-Jurgen Buschmann, Eckhard Schollmeyer. "Modifizierung von Faseroberflachen durch die permanente Fixierung supramolekularer Komponenten, Teil 4: Fulleren C60." Die Angewandte Makromolekulare Chemie 258 (1998) 87-91 (Nr. 4546). German with English Summary. (Year: 1998).*

(Continued)

*Primary Examiner* — Isaac Shomer

(57) ABSTRACT

The present invention relates to a bioactive or real-time and pathogen killing material comprised of a carbon nanostructure (preferably a fullerene but including other functionalized carbon-based nanostructures) that possess potent broad-spectrum antimicrobial properties. The present invention relates to the utilization of functionalized carbon nanostructures as a bioactive antimicrobial substance that is incorporated into a material, including a textile, fabric, solution, salve, or cream. The preferred embodiment of the present invention is fullerene derivatives that are chemically functionalized on the cage with a halogen element. The present invention pertains to a material that is suitable for barrier garments, accessory garments (shoe covers, masks, facial visors, etc.), textiles (bed sheets, blankets, towels, personal clothing, gowns, surgical drapes, curtains, drapes, pads, etc.), filtration matrices (for use in hemodialysis, hemofiltration, etc.), or aerosolized solutions, sprays, liquids, salves, (Continued)

or creams. The present invention further relates to a production method thereof.

9 Claims, 6 Drawing Sheets

(51) Int. Cl.
  *B82Y 5/00* (2011.01)
  *C01B 32/152* (2017.01)
  *A61K 33/44* (2006.01)
  *A01N 59/00* (2006.01)
  *A61M 1/36* (2006.01)
  *A61K 9/00* (2006.01)
  *B82Y 40/00* (2011.01)
  *A61K 9/08* (2006.01)

(52) U.S. Cl.
  CPC ............ *A61K 9/006* (2013.01); *A61K 9/0043* (2013.01); *A61K 9/08* (2013.01); *B82Y 5/00* (2013.01); *B82Y 30/00* (2013.01); *B82Y 40/00* (2013.01); *C01B 32/152* (2017.08)

(56) References Cited

U.S. PATENT DOCUMENTS

| | | | |
|---|---|---|---|
| 7,862,624 | B2 | 1/2011 | Tran |
| 9,289,450 | B2 | 3/2016 | Burton et al. |
| 2005/0229328 | A1* | 10/2005 | Tran ...................... D06M 16/00 8/115.51 |
| 2011/0123757 | A1* | 5/2011 | Howland .................. A62D 5/00 428/85 |
| 2011/0232653 | A1* | 9/2011 | Imashiro .............. A41D 31/305 128/863 |
| 2012/0122695 | A1* | 5/2012 | Naseri ..................... A61P 17/00 504/359 |
| 2013/0041185 | A1* | 2/2013 | Kokubo ................. B82Y 30/00 568/808 |
| 2014/0138612 | A1* | 5/2014 | Virkar .................... B82Y 40/00 257/9 |
| 2015/0011802 | A1* | 1/2015 | Kokubo ................. B82Y 40/00 568/817 |
| 2019/0141996 | A1* | 5/2019 | Wada .................... A01N 25/34 424/404 |

OTHER PUBLICATIONS

Sheila Shahidi and Bahareh Moazzenchi. "Carbon nanotube and its applications in textile industry—A review." The Journal of the Textile Institute, vol. 109, No. 12, 2018, pp. 1653-1666. (Year: 2018).*

Fanica Cimpoesu, Nita Dragoe, Harry Ramanantoanina, Werner Urland and Claude Daul. "The theoretical account of the ligand field bonding regime and magnetic anisotropy in the DySc2N@C80 single ion magnet endohedral fullerene." Physical Chemistry Chemical Physics, vol. 16, 2014, pp. 11337-11348. (Year: 2014).*

Anthony Dellinger. "Fullerenes and their Potential in Nanomedicine." PhD Thesis, University of North Carolina at Greensboro, 2015, pp. ii-xi, 1-143, and an initial sheet. (Year: 2015).*

* cited by examiner

SYNTHETIC, MULTIFACETED HALOGENATED, FUNCTIONALIZED FULLERENES ENGINEERED FOR MICROBICIDAL EFFECTS EMPLOYING CONTROLLED CONTACT FOR SAFE THERAPEUTIC AND ENVIRONMENTAL UTILITY

CROSS-REFERENCE TO RELATED APPLICATION

This application claims priority to U.S. Provisional Patent Application Ser. No. 63/013,125 filed by Brady, Dellinger, Robertson, and Tinker-Kulberg on Apr. 21, 2020, entitled "Bioactive/antimicrobial, non-disposable personal protection equipment that safely kills viral, bacterial and fungal matter upon contact."

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

STATEMENT REGARDING PRIOR DISCLOSURES BY THE INVENTOR OR A JOINT INVENTOR

Not applicable.

BACKGROUND OF THE INVENTION

Field of the Invention

The present invention relates to a resilient and enduring article comprised of a nanomaterial-based antimicrobial agent and a method for preparing such articles. Said article is imbued with carbon nanostructures that destroys pathogens, as well as preclude proliferation and inhibits growth of microorganisms. Such carbon nanostructures are preferably halogenated fullerenes (halofullerenes) that, upon contact of the article with a broad-spectrum of pathogens in air, vapor, biological and physiological fluids would exert a rapid antimicrobial effect. Halofullerene integrated articles associated with the present invention includes, but are not limited to clothing/garments, protective equipment, upholstery materials, filtration matrices, or any affinity or non-affinity surface using a litany of bonding or attachment techniques including immunochemistry and otherwise utility in solution, gas or atomization of particles when and where pathogenic control or destruction is desirable. Halofullerenes are incompressible and in these applications, permanent, neither losing their anti-pathogenic properties or shape or size with repeated and long-term use while retaining bioactivity.

Description of the Related Art

Global interest in functional materials with antimicrobial activity have surfaced to the forefront during the 2020 global COVID-19 pandemic. Medical personnel, infectious disease experts, and consumers seek a wide range of textile products with robust, durable and effective antimicrobial properties. These necessities are instrumental in the healthcare environment where healthcare-associated infections (HAI) are prolific. The introduction of novel surveillance and stewardship policies have been introduced to mitigate growing trends associated with pathogen transmission and infectious disease outbreaks in all environments. Paradoxically, personal protective equipment (PPE) and safety garments are designed to protect individuals from pathogens, however conventional articles have contributed to transmission and spread in these highly pathogenic environments. Such circumstances are traditionally related to the nature and design of the article, which functions as a barrier material that prevents wearer contact with circulating pathogens. Most of the current art is comprised of inert hydrophobic materials that impede or prevent pathogen penetration into the article. As such, the possibility for spreading pathogens throughout the environment is enhanced by these materials. Predominantly, this occurs via passive transmission, involving the direct transference of a pathogen from a contaminated article to another surface (i.e. skin, doorknob, shoes, railing, walls, instruments, etc.), as well as via airborne respiration of a contagion. Recent surveys from Virginia Commonwealth University indicated that 62% of hospital staff that donned traditional PPE (coats), only washed these articles once every two weeks, despite daily wearing. Irrespective of washing frequency, in a highly pathogenic environment, these materials can become fully contaminated in as little as an 8-hour period. Synthetic barrier garments without microbocidal properties allow for the accumulation of airborne and surface microbes and subsequent distribution along the pathways of workers comings and goings in airstreams and contacts. Antithetically, HAIs have grown much more prevalent and common, coinciding with inexpensive and synthetic PPE replacing washed or sterilized cotton gowns.

Furthermore, wearer susceptibility to environmentally scavenged and collected pathogens is notable during periods of de-garmenting or changing, when these individuals are faced with direct exposure or contact with the captured and viable material on the article. As such, many studies have indicated that pathogens remain viable on most traditional barrier articles or upholsteries for as long as one month. Thus, novel bioactive and functional antimicrobial finishes and treatments for common textiles can play a key role in reducing transmission and spread of pathogens. Beneficial protective articles should function as a repository for circulating environmental pathogens, adsorbing them on the surface as well as imparting an antimicrobial mechanism on the captured pathogens that kills and reduces secondary spread and transmission. In the case of global air borne viral pandemics, all of these tenants extend beyond the healthcare environments and are relevant in every façade of society.

Antimicrobial agents are compounds that inhibit the growth of and/or kill microorganisms. Numerous commercial products possess a wide range of antimicrobial properties. However, many such compounds have a truncated antimicrobial spectrum and/or may be incompatible for materials that come in contact with the wearer. Equally problematic, the antimicrobial effect of many compounds can gradually diminish overtime, resulting in lost activity, especially during repetitive wearing or laundering (leeching). Of additional concern, some compounds, when utilized routinely may result in reduced efficacy, imparted by bacteria adaptation and resistance. As such, durable antimicrobial materials that possess broad spectrum and persistent pathogen killing mechanisms that can withstand rigorous use and laundering and are biocompatible/safe are urgently needed inventions.

Fullerenes represent one possible inclusion in this space. Fullerenes are spherical, novel allotropes of carbon that are currently being pursued globally for a wide range of applications in nanomedicine. The molecules represent a novel compound for development of a functional and bioactive antimicrobial article. Fullerenes possess unique electronic properties that make them attractive candidates for numerous medical applications. The innate properties of fullerenes render high antioxidant capacity at extremely small sizes with substantial surface area that can be further functionalized or engineered to accommodate a broad range of applications.

The small size (<5 nm) of the fullerene and the ability to modify their carbon cage with countless external moieties provides the framework for next generation nanomaterial applications and inventions. The use of fullerenes has shown profound therapeutic potential as a cellular stabilizing agent, free-radical sponge, anti-inflammatory, antiviral, antibacterial, antifungal, as well as numerous different applications. Endohedral fullerenes, those with encapsulated atoms, ions or cluster have shown exceptional promise as contrast agents, capable of targeting a specific cell type (i.e.: cancer) or host environment (i.e.: atherosclerosis and inflammation) and improving diagnostic imaging capabilities and sensitivities.

While the small size and functionality of the fullerene define the properties of molecule, these features have impeded meaningful medical adoption to date. The potential for using fullerene-based medicines is substantial but concerns of toxicity have slowed the initial enthusiasm that surrounded their discovery. As such, these molecules have been unable to cross the biological Rubicon because of regulatory limitations associated with characterization of an infinitesimally small molecular entity and a technical/analytical inability to fully evaluate the risk, toxicity, clearance, absorption, elimination, metabolism, etc. Despite promise and significant global research and development outcomes for numerous biological applications, these limitations have been major obstacles for introducing fullerenes into biology and medicine.

Each of the challenges that have been prevented the integration of fullerene into modern medicine is directly related to systemic administration of the fullerene in the host and the inability to fully characterize the materials biological fate, systemically.

In the case of this patent, the pathogenic properties of the fullerene would be harnessed without placing the functional article into direct contact with the host's blood stream, but rather by decorating or coating external material that would leverage the antimicrobial capabilities of the fullerene in the environment surrounding the wearer in a PPE application and therapeutically with microbocidal utility but without particle release into the bloodstream or atmosphere. Furthermore, high fullerene production costs have historically created significant barriers for viable economic industrial applications. Today, these prices have dropped markedly are continue to very rapid decline, ushering in a viable commercial opportunity for these molecules as proposed in this patent.

U.S. Pat. No. 2,791,518A—Process for making a microbicidal article, issued May 7, 1974 to Stokes and Davis, describes methods and treatment for the soaking of an article, such as a textile with an aqueous antimicrobial solution containing a water-soluble basic nitrogenous compound and a silver salt, followed by a second soaking that comprises a water-soluble halide or phosphate and a water-soluble salt, which may also be a phosphate. In contrast to the proposed patent, U.S. Pat. No. 2,791,518A does not teach the art of introducing a permanently affixed halogen-functionalized fullerene derivative (FD) to the article. Accordingly, the method for making said antimicrobial article described by Stokes and Davis would possess momentary antimicrobial activity upon application but would not be lasting or continuous. Subsequently, laundering or washing of the article would result in diminished or reduced antimicrobial capabilities. These shortcomings associated with the art taught by Stokes and Davis are addressed in this patent submission.

U.S. Pat. No. 4,721,511A—Leach resistant antimicrobial fabric, issued Jan. 26, 1988 to Kuptis teaches a leach resistant antimicrobial fabric comprised of a nonwoven substrate and a silicone quaternary amine. In one embodiment Kuptis teaches a bioactive, water-repellant, alcohol-repellant fabric containing a fluoropolymer and a non-leaching antimicrobial amine. Another embodiment of Kuptis, teaches a non-repellant fabric containing alkoxysilane quaternary amine with an aromatic carbon chain of 11-22 carbons functionalized with a chlorine or bromine. In contrast to the proposed patent, U.S. Pat. No. 4,721,511A teaches a hydrophobic article as a repelling surface. The association of hydrophobicity on the surface of a protective garment does not adequately address the ability to prevent transfer of a pathogenic liquid material (i.e: air vapor, saliva from a sneeze or cough, mucus, blood, or similar potentially contaminated biological or non-biological liquid substance). The repellant shortcoming is addressed in this proposed patent by utilizing a highly hydrophilic article that is further coated with an ultra-hydrophilic polymer to adhere and adsorb pathogen-contaminated liquid material of biological or non-biological nature. Kuptis further teaches the art of an antimicrobial sidechain that is comprised of a bromine or chlorine and attached to a silyl quaternary amine compound (QAC) previously described in U.S. Pat. No. 3,730,701A—Method for controlled growing of algae in an aqueous medium, issued May 1, 1973 to Isquith et al. The mode of antimicrobial action of QAC is via disruption of the cellular membrane. Exposure of pathogens to QAC compounds has resulted in genetic mutations in the microorganism that reveal resistance to QACs. The shortcomings associated with a singular mode of action is addressed in this patent via the inclusion of halogen FD that would impart antimicrobial effects associated with variations in functional groups (R—) including fluorine, iodine, bromine and chlorine moieties. Further differentiation from Kuptis is realized by the electronic properties intrinsic to the fullerene. Fullerenes have a unique cage structure with delocalized π-molecular orbital electrons, which confers unusual activity in electron transfer systems due to their low reorganization energy, low lying excited states (singlet and triplet) and extended triplet lifetimes. Furthermore, the spherical configuration of the planar benzene rings imposes an unusual constraint on these π-electron orbitals. The carbon cage of fullerenes readily, constantly and regeneratively absorbs and disperses electrons. This characteristic of the fullerene is highly toxic to pathogens because organisms lack a nuclear membrane that protects their genetic material. Free electrons released from the fullerene cage come into direct contact with the pathogen and due to a lack of a nuclear membrane, this oxidative stress damages the cellular genetic material, impede proliferation and kills the microorganism.

China Pat. No. 1,145,415C—Durable and regenerable microbicidal textiles, issued Apr. 4, 2004 to Sun et al. teaches a durable and regenerable microbiocidal textiles and methods for preparing such textiles. In one embodiment, Sun teaches a textile precursor, cellulose, cellulose/polyester and polyester, immersed in an aqueous treatment solution, comprised of heterocyclic N-halogenated amine that is dried and cured. The preferred halogenated solution can be solutions of chlorine or bromine. The preferred halogenated solution is chlorine, such as bleaching liquids (i.e.: Clorox). This antibacterial agent is connected to the surface of the textile via a covalent bond to improve durability. Briefly, the textile is soaked in the antimicrobial solution, excess aqueous solution is removed (via pressing, compression, rolling, or centrifugation), heated to dry between 50° C. and 90° C. for 3 to 8 minutes, and subsequently heated at a solidification between 120° C. to 180° C. for 3 to 8 minutes in a pressurized oven. The cellulose bound antimicrobial solution is covalent, stable for washing, and insoluble. The final treated and processed fabric contains 0.01% chlorine with gram-positive and gram-negative antimicrobial capabilities. The use of a fungicidal compounds is also taught by the art. The proposed patent differs from the work presented by Sun et al. in antimicrobial mechanism and article maintenance. The covalently bonded antimicrobial agent in U.S. Pat. No. 1,145,415C is a free chlorine molecule that interacts with a halogenated amine attached to a cellulose strand on the article and affixed. The antimicrobial mechanism is associated with the interaction of the chlorine molecule with a pathogenic material and requires regeneration after use with a chlorine-based detergent to recharge the covalently bonded amine structure that is attached to the cellulose. In the proposed invention, the antimicrobial material is imbued in the article via entrapment and exploitation of the elastomeric memory of the article. Further, the fullerene imparts a multiple antimicrobial capability via release of electrons across the outer shell that can damage the genetic material of the invading pathogen, as well as the caustic properties of the functionalized halogen material on the side chain. The functional material affixed to the fullerene can be comprised of chlorine, bromine, iodine or another suitable halogen molecule and remains stably attached to the fullerene.

Korean Pat. No. 102,085,345B1—Textiles with antimicrobial properties, issued Mar. 5, 2020 to Swami et al. teaches the method for manufacturing a wash durable, non-leaching treated textile with antimicrobial activity. In one embodiment, Swami teaches the process of drying and curing a textile treated with two or more antibacterial agents selected from the group consisting of QAC at various weight percentages. In one embodiment, the QAC may contain an anion, particularly a chloride, bromide, fluoride, iodide, acetate or sulfonate group, preferably chloride or bromide. The antimicrobial compounds are covalently attached to the textile material via the organosilane residue and the functional group of the textile, in a non-leaching manner. The proposed patent differs from the art taught by Swami et al. in that the antimicrobial material is impregnated into the garment, exploiting surface features on the article and conformational, temperature-induced changes to the material that behave to capture and contain the antimicrobial nanomaterial inside the cavities of the article. The art presented by Swami et al. leaves microbes without affinity to the surface (hydrophilic surface action) and suffers the same characteristic of synthetic PPE. Most pathogens are aqueous, especially microbes in exhaled air, when humans are the disease vector or source of contagion. Atomic scale interaction is vital, specifically regarding airborne virus in exhaled, moist breath. Ultra-hydrophilic properties easily overcome the airborne dynamic of an air-floating pathogen particularly very small virus.

U.S. Pat. No. 9,289,450B2—Silver-containing antimicrobial articles and methods of manufacture, issued Mar. 22, 2016 to Burton et al. teaches a porous or nonporous article that is coated with silver sulfate or other silver metal compounds. The methods further explain a technique for whitening, via radiation, the article or a portion of the article to prevent silver induced color changes or staining. The intended use of the antimicrobial product is as a medical article, preferably for wound bandaging or dressing. The silver compounds impart antimicrobial effects to a surface with minimal risk of developing bacterial resistance. In the wound bandage or dressing, silver is delivered to the surface by sustained release of silver ions from the surface when in contact with moist environments, such as a wound bed. The art taught by Burton is a silver coated article that leverages the antimicrobial properties of silver ions released by the coating. Burton does not teach a method to manufacture an article with persistent antimicrobial capabilities and the article would require intermittent exposure to or soaking in a silver containing solution over time to preserve article function.

The functionalization chemistry for fullerene nanomaterials has been extensively researched since the early in 1990s. Two approaches were developed to increase the solubility of the fullerene in aqueous solutions. The first method, required the utilization of a solubilizing agent such as poly(N-vinylpyrrolidone), however the second method, which relied on the introduction of hydrophilic function moieties via chemical modification became the accepted approach (for ease and simplicity). Since these discoveries the inclusion of halogen molecules, as well as numerous other moieties have been published in the literature and proven effective. The Bingel, Bingel-Hirsch, Prato and azoalkane cycloaddition reactions are the most common functionalization methods, but many innervations have materialized over the last 27-years. A recent example of advancements in fullerene functionalization research is shown in Kraevaya et al. "inversed Arbuzov reaction of the fullerene derivatives that resulted in halogenated, water-soluble fullerene compounds that demonstrated promising antiviral activities" (Org. Biomol. Chem., 2019, 17, 7155). This method teaches highly functionalized and pure fullerene structures with halogen molecules at various degrees.

In U.S. Pat. No. 7,862,624B2—Nano-particles on fabric or textile, issued Jan. 4, 2011 to Tran, the inventors discuss the systems and methods for fabricating a wash durable material comprised of strands with void spaces in the strands that are filled with nano-particles. The art describes a substrate (yarn, textile, fabric or film) that is embedded with nanoparticles (silver, gold, aluminum) to provide one of several characteristics: antimicrobial, odor-reduction, heat retention, fireproofing, distinct colorations, reduced discolorations and improved material strength and resistance to sharp edges. The void volumes of (and between) the fiber strands are at least partially filled with particles smaller than 100 nm. The nanoparticles introduced to the void volumes may be of homogeneous composition or comprised of plurality compositions of nano-particle types. The article may include woven and non-woven fabrics, of natural or synthetic origin, or blends thereof. Fibers may additionally include continuous or discontinuous monofilaments, multifilaments, staple fibers, and yarns of any desired composition. The fibers can be natural, manmade, synthetic, or mixtures thereof. Nanoparticles are applied to fiber via soaking, spin casting, dipping, fluid-flow, padding, or spraying. Upon application, the substrate with the nanoparticles is dried at room temperature. The nanoparticles are capable of contracting and/or expanding at predetermined temperatures and substantially remain after the substrate is washed at least 40 times. In the proposed patent, Tran teaches a method of applying a silver, gold, or aluminum nanoparticle to an article. The art leverages the expansion of the nanomaterial applied to the article, whereby the particles expand or contract at predetermined temperatures and become imbedded in the article voids. The patent proposed herein differs from Tran by using the shape memory retention characteristics of the article, which can be influenced by temperature, whereby the article expands to accept the FD and can be contracted to capture the FD.

BRIEF SUMMARY OF THE INVENTION

The present invention is directed to a halogenated fullerene nanomaterial modified antimicrobial article and a method for manufacturing the article. Fullerenes are carbon spheres that measure less than 100 nm. The carbon cages of the fullerenes are capable of modification via chemical functionalization of specific and selected side-chain moieties. The plethora of possibilities for fullerene functionalization represents a broad range of functional derivatives with valuable properties and potential for practical application in society and medicine. In the present invention, fullerenes are functionalized with potent halogen molecules, including chlorine, fluorine, bromine and iodine, which are known to impart and enhance the antimicrobial capacity of composite.

Empty cage fullerenes have unique electrochemical properties and have a wide range of potentially beneficial biologic properties. Another type of fullerene can have magnetic metals enclosed inside them (endohedral fullerenes) and typically used as a contrast agent. Fullerenes have a cage structure with delocalized $\pi$-molecular orbital electrons. This structure confers extraordinary activity in electron transfer systems due to their low reorganization energy, low lying excited states (singlet and triplet) and extended triplet lifetimes. Furthermore, the spherical configuration of the planar benzene rings imposes an unusual constraint on these $\pi$-electron orbitals. The native fullerene cage is insoluble in water and must be functionalized. A functionalized fullerene, or fullerene derivative (FD), represents a chemical process of attaching a molecule or moiety to the outer cage of the fullerene. Such functionalization can impart unique and/or enhanced properties to the native carbon sphere. These functionalities can be leveraged to exploit specific properties, enable specific or targeted localization, and render the fullerene water soluble (requisite for compatibility in biological systems). The ability of fullerenes to be functionalized with side chains provides opportunities to diversify, manipulate and harness the electronic properties of the cage for specific and selected applications. Each derivation results in changes of the compound's physical and chemical properties, including particle size/length, zeta-potential, molecular weight, surface characteristics and solubility, all of which contribute to how molecule affects biological systems. Even extremely similar FD can have completely opposite biological results, based on the fullerene chemical composition, structural arrangement and molecular interactions at the cellular, tissue and organ system levels. All posing challenges, when considering the FD as a biological substance that is administered systemically.

Fullerenes have been coined 'free radical sponges' and described most frequently as antioxidants, although in biological systems fullerenes unexpectedly behave as both oxidants and antioxidants. The generation of free radicals such as reactive oxygen species (ROS) and reactive nitrogen species (RNS) occurs naturally in cells, and their presence at sites of disease pathologies suggests that these entities (ROS and RNS) contribute to disease progression. The term free radical refers to a molecular species that possesses an unpaired electron, which makes them highly reactive. Many of the more common ROS or RNS that contribute to oxidative or nitrosative stress in biological systems are free radicals, including hydroxyl radicals (OH.), superoxide anions (O—), and peroxynitrites (ONOO—). These ROS can react with, crosslink and alter the function of many molecules. These species can negatively affect a variety of biological processes.

This radical scavenging property of fullerenes allows for the ability to take up an electron from radicals (an ongoing organic decay process with microbes). On the atomic scale the ability to exchange an electron is an energy process that occurs without direct contact with the fullerene (as atoms are in motion) and therefore a fullerene has a natural affinity to proximal radicals including the ones circumspect to pathogens. Essentially, fullerenes have a natural attraction to microbes because of radical oxygen decay, which is occurring continuously in the microbial life form. The fullerene would work to draw a pathogen toward the carbon nanomaterial's orbital during the electron exchange using natural atomic forces. These physical properties of the fullerene represent a stable and broad-spectrum molecule with high binding affinity to all pathogens (which typically possess negatively charged cell walls).

The carbon cage of fullerenes has tremendous functionality based on its ability to absorb electrons and disperse them through the 3D $\pi$-conjugated structure distributed over its surface. In the present invention, the fullerene cage is vital because the actual mass is on the atomic scale (1-100 nm) but arranged in a geodesic configuration of hollow/empty space. The bulk of space occupied by fullerenes is overtly "negative," offering a species with tremendous surface area but absent any meaningful mass. This characteristic is vital to this invention due to aspects articulated below.

The functionality of the fullerene and ability to be modified with or bonded to a second molecule that is highly antimicrobial has remarkable opportunity. The use of specific chemical reactions that results in the generation of halofullerenes, or a functional fullerene cage possessing multiple side-chain halogens (i.e.: iodine, bromine, chlorine and fluorine) renders a bioactive nano-scale antimicrobial agent. Principally, with respect to this invention, the high pathogen affinity with the halogen FD represents an inescapable antimicrobial atomic field. Thus a halofullerene would demonstrate molecular affinity towards and attraction of pathogenic species and functionalization with highly antimicrobial halogens that caustically kill a microbe instantaneously, without losing any energy, virulence or the ability to maintain a continuous antimicrobial capability.

At present, the utilization of fullerenes is being researched and pursued globally for a wide range of applications in medicine, however the ability to fully characterize these nanoscale molecules has stymied adoption. These limitations are partly a result of the lack of standard structural relationships that affect biological outcomes of FD. In addition to poor characterization methods, the toxicity considerations for nanomaterials has been the subject of significant debate for more than 30 years. Numerous studies examining the toxicity of fullerenes and FD have resulted in conflicting and inconclusive results. Complicating the task of introducing fullerenes and FD into the medical space is the fact that the FDA does not have specific guidelines for products containing nanoscale materials. A report issued by the FDA Nanotechnology Task Force (July 2007) recommends guidance by various centers within the FDA for industries working with nanomaterials. In the report the FDA stressed that valuable information on the biodistribution of nanoparticles and possibly accumulation sites are lacking. Importantly, most drug safety standards assess a molecule's half-life or half-life of chemically formed metabolites of the molecule. Conversely, the robust structural stability of the fullerene makes extrapolating half-life a near impossible task. Due to the inherent size and properties of the fullerene and limitations associated with analytical instrumentation, accomplishing such recommendations has ranged from challenging to analytically impossible. As such, establishing appropriate endpoints for in vitro assays are difficult to determine, as single cell types are often not sufficient for evaluation on the function or health of organs or tissues that are comprised of multiple cell types, and given that numerous types of tissues are exposed to in the body appropriate assessments of safety guidelines for fullerenes in biological systems have failed to materialize. This patent has devised a method that would integrate the FD into practical application by eliminating the uncertainty associated with systemic distribution of the nanomaterial, but rather incorporating the FD into applications that would not cross the barrier for systemic release.

This invention uses physical properties and propensities of matter that addresses microbes without the benefits of a host environment. Physical properties include gravity, hydrophilic and hydrophobic material characteristics, hydroscopic or osmotic affinity, particle laminar flow, and environmental molecular particulars on a micro- and nanoscale on strictly atomic dimensions.

An airborne pathogen emanating from an infected host in the form of a cough or sneeze (by example) is viably limited without a new host. Specifically, these opportunistic pathogens must be presented with and enter into a new host system, with notable pathogenic abundance to survive and replicate. Once the host is infected, pathogen proliferation can quickly overwhelm antigenic defenses like white cells or other immunologic responses. Thus, the need to mitigate the pathogen load or abundance is paramount and logical for numerous environments.

Pathogens require a host to survive and grow, without such a host these microorganisms become extraordinarily vulnerable in rapid succession. Surface features and physical environments can perforate or puncture the cell wall of the pathogen, resulting in immediate loss of form and function. Most commonly, pathogens are killed with antimicrobial chemistry and gases that caustically disrupts the tissue that protects the intracellular genetic material of the microorganism (in the form of DNA or RNA). Corrosive, caustic material can disrupt tissue and cellular integrity resulting in death of the pathogen. Some pathogens are double walled (gram-negative bacteria) and are technically more difficult to damage and kill. In another case, the pathogens readily adapt to antibiotics and become resistance to the drugs ability to kill the pathogen. Viral pathogen integrity is not susceptible to antibiotics and biologically requires antiviral substances that are highly, mono-specifically engineered to target a protease weakness (or other pathway) in specific viral pathogens. Typically, drug engineering for virus species is specific and only monolithically effective towards one virus type, but not considered broad spectrum. This aspect of killing virus without harming the host is overwhelmingly challenging. Vaccinations for viral disease like seasonal flu require a highly specific antibody (immunologic response) such that the exact species of virus is targeted.

Pathogens of any ilk, bacterial, fungal or viral are highly susceptible to powerful antimicrobial matter assuming that the chemistry can come into direct contact with the pathogen. In a household sense, ordinary bleach will kill these pathogens instantly on contact. Highly dilute bleach will likewise kill these pathogens even if the contact time must increase proportionally to the concentration. Iodine at very low concentrations readily kills pathogens instantly. Notably, simple dehydration will kill most pathogens.

As a species, nearly all microbes are predominately aqueous. The features associated with the natural characteristics of a predominately aqueous material include: relaxitivity, temperature and ease of deformability. For example, when water contacts an ultra-hydrophilic material the substance immediately yields to that physical force and is consumed by the substance. Capillary action is the ability of a liquid to flow in narrow spaces without the assistance of (or opposition to) externally imposing forces like gravity. Thus, a droplet of water (emitted from a person via a sneeze or cough) rich in pathogenic matter, would be subject to capillary action and the microorganisms contained within aqueous phase would travel along with the force of the water naturally and unabated via capillary energy. This is attributable to the bulk of water compared to the miniscule size and weight of microbes. It is notable that capillary action works handily on liquids as viscous as mammalian blood, ±50% water, as well. Blood, mucus, saliva and other biological fluids are equally susceptible to capillary action notwithstanding lower water content. Pathogenic content of the viscous fluid material would follow the water extraction aspects as opposed to the putrid solids notwithstanding the ubiquity of pathogens.

The development of a highly hydrophilic article permanently infused with antimicrobial FD has significant merit from a bioactive and functional position. The nature of the material, hydrophilic, would draw in aqueous phase pathogenic material and the physical properties of these interactions would serve to align and present the pathogen with a profound antimicrobial moiety permanently affixed to the article. The combination of hydrophilic interactions and electronic properties of the garment, the FD, and the pathogenic material work coordinate antimicrobial action. Upon pathogen adsorption on the article, the vehicle (liquid) containing pathogenic matter is drawn inward and the FD would attract the microorganism in space towards the molecular orbital. Once proximal, the presence of halogens decorating the fullerene and the unique electronic properties of the FD would impart a multifaceted pathogenic mechanism that disrupts the cellular membrane and genetic material of the pathogen, resulting in death. The mode of action, electron emissions from the fullerene cage and affixed caustic halogens to the fullerene cage would be persistent and facilitate profound antimicrobial capabilities over time, irrespective of pathogen type or concentration.

BRIEF DESCRIPTION OF SEVERAL VIEWS OF THE DRAWING

FIG. 3A illustrates the relaxed void at an increased temperature when halofullerenes would be applied. FIG. 3B illustrates the undeformed void after cooling to ambient temperature and entrapping the halofullerenes within.

DETAILED DESCRIPTION OF THE INVENTION

Figure 1A:
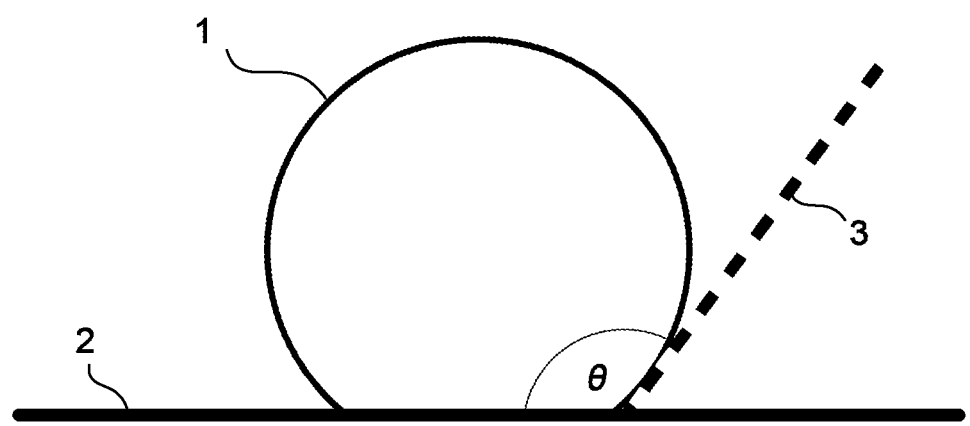
FIG. 1A is a side cross sectional view of a typical hydrophobic article and FIG. 1B is a cross sectional view of ultra-hydrophilic coated article according to an embodiment of this invention, wherein a thin hydrophilic coating is applied to the article.

For the purpose of invention, the term "pathogen" describes microorganisms including, but not limited to, bacteria, protozoa, viruses, molds, yeasts, fungi and the like. The term "antimicrobial" is intended to convey the propensity to inhibit, prevent, or destroy a pathogen, as well as preclude proliferation and growth of a microorganism.

From an infectious disease outlook, pathogens are transmitted through contagion and require a host organism to survive and proliferate. Similarly, pathogens are unable to survive numerous antimicrobial processes. Most pathogens are highly aqueous in nature and airborne pathogens can remain active and viable outside of the host, however the organisms are not shielded or protected in the gas form and are especially vulnerable. These lightweight particles can linger or diffuse in the air for different periods of time, largely dictated by temperature and humidity. These characteristics of a pathogen enable airborne transfer, however their vulnerability outside of the hosts represents an opportunistic method for elimination with a bioactive and functional antimicrobial article.

Briefly, the proposed invention is to impregnate an article with halofullerenes or use the particles in a controlled and inescapable manner, therapeutically. The antimicrobial potency of the fullerene and linked halogen molecule(s) coupled with the regenerative nature of the fullerene renders the article an inexhaustible pathogen killing magnet upon contact. Secondarily, the article is coated with an ultra-hydrophilic polymer that synthetically creates molecular space that attracts and adsorbs water or moisture (moisture rich microbe). Microscopic hydrophilic voids are shaped to attract and retain water (until evaporation). The hydrophilic polymer coated article would draw pathogenic materials towards the article and into the surface voids, which are imbued with an abundance of spatially trapped FD. Once a pathogen contacts the garment it is immediately pulled into the cavities that are loaded with antimicrobial FDs. Within these voids the aqueous pathogenic material would surface contact a concentration of FDs that stimulate pathogen death in rapid succession. In this embodiment, the pathogen is subjected to three lethal forces at the atomic level: inescapable hydrophilic energy, electron exchange and caustic halogen.

The proposed article material may be comprised of hydrophilic fabrics such as cotton, wool, linen, silk, nylon blends, and blends thereof and sometimes liquids. The article is further subject to an ultra-hydrophilic polymer coating that is polymeric and has elastomeric characteristics reactive to specific temperature gradations. The ultra-hydrophilic polymer coating is comprised of polymers or copolymers of: acrylic acid (PAA), polyvinyl alcohol (PVA), polyvinyl pyrrolidone (PVP), polyethylene oxide (PEO), methacrylic acid (PMA), itaconic acid (PIA), propylene oxide and ethylene oxide [P(EO/PO)], maleic acid (PLA) and 3-butene-1,2,3-tricarboxylic acid (PBA), or combinations thereof. An additional aspect of the proposed invention is to make the article rugged and enduring in a demanding environment without losing the antimicrobial properties. This includes routine washing and drying without harm to the hydrophilic properties of the article or dissociation of the FDs from the article. Thus article design must ensure that the FDs do not fall out of the voids or are not destroyed by laundering. As such, the initial coating of the article would be performed at a relatively high temperature (65.5° C.) such that the initial dried state of the hydrophilic coating is slightly larger than at cooler temperatures (i.e: room temperature). Thus, the hydrophilic void diameter is slightly smaller than the original normo-thermic at the coating step. Additionally, the hydrophilic voids are filled with FDs. After inclusion of FDs, the article is gradually cooled to a low temperature (0° C.), thereby shrinking the polymer, yet increasing the void volume. Upon air drying of the material, using a dehumidifying process, the temperature can be slowly raised to ordinary room temperatures without material deformation. The polymers expand and void space decreases and consequently the FDs are trapped inside of the void. The halogen sidechains of the fullerene cage act in a cross-hatching feature better trapping the bonded FDs inside of the article cavities.

The entire process renders the garment polymeric and resistance to soiling and capable of routine and easy washing without loss or escape of impregnated FDs. The primary hydrophilic nature of the article remains the predominate feature, even though microscopically the fibers are coated with a polymer resistant to staining or soiling.

In one embodiment, the present invention provides a method of manufacturing a protective antimicrobial article, that is a garment for wear routine wear. Examples of this embodiment include PPE, apparel, and accessory garments, including, but are not limited to gowns, shirts, gloves, masks, shoe covers, and other types of clothing material. Alternatively, in another embodiment, the antimicrobial coating composition is usable in a wide variety of textiles. Such textiles include, but are not limited to, sheets, table covers, linens, pads, drapes, towels, dressings, bedding material and other upholstered structures common to healthcare, household, travel, and hotel settings.

Contemporary PPE and textiles are hydrophobic and do not absorb moisture, as such the material functions as a moisture repellent. The nature of hydrophobic articles provides barrier protection but imparts little direct benefit for the control of pathogen elimination or transmissibility. As shown in FIG. 1A, the contact angle (8) of a liquid droplet (1) on a surface (2) is shown, this relationship is directly associated to the physical properties of the material. Whereby, a hydrophobic surface (2) has contact angle (8) with water that is greater than 90° (3). Upon contact with a droplet (1), hydrophobic articles function to repel the droplet (and pathogenic material contained inside the aqueous suspension) such that the liquid is not adsorbed into the material (2). These hydrophobic interactions illustrate a possible mechanism for transference of viable pathogenic material by allowing continued transference throughout the environment.

Figure 1B:
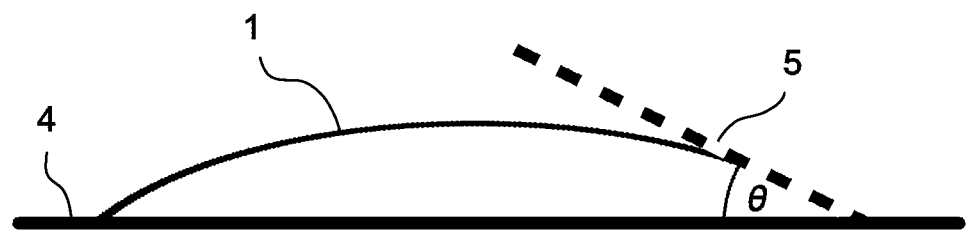

As shown in FIG. 1B, the conventional definition for a hydrophilic surface (4) is described as the surface-water contact angle (8) being less than 90° (5). In this proposed patent a hydrophilic article is coated with an elastomeric ultra-hydrophilic polymer (4) that enhances the adsorption of aqueous material (1) into the article. This affinity with water functions to reduce the likelihood of transference of pathogen from the article to another surface.

Figure 2:
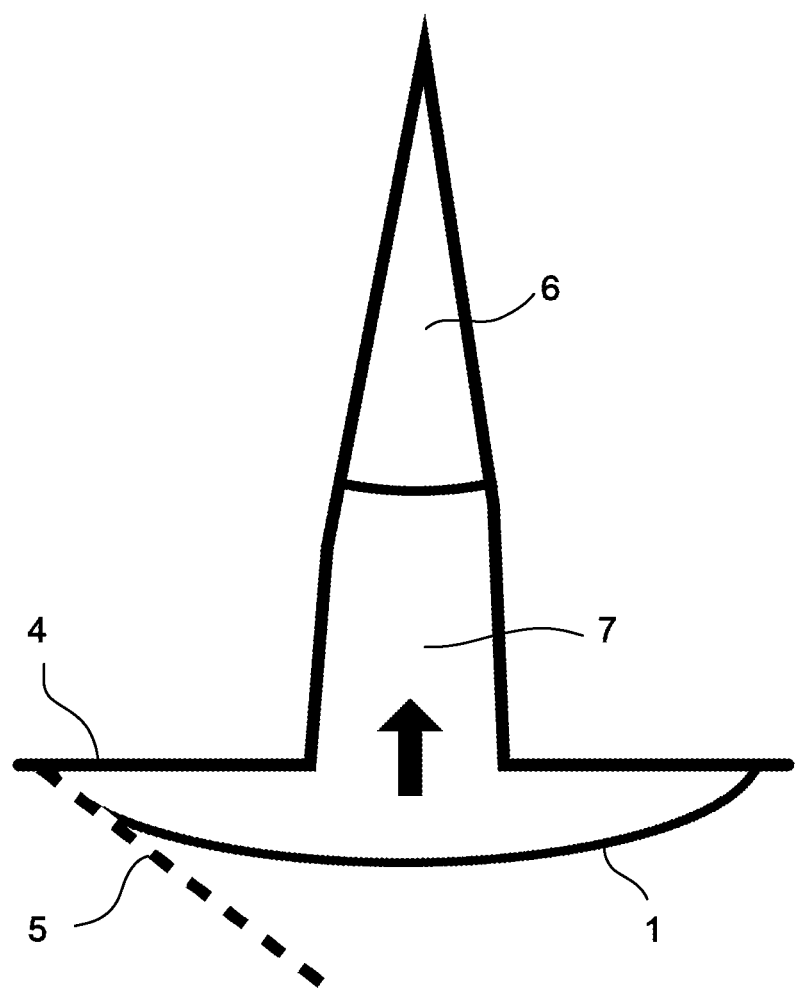
FIG. 2 represents a cross sectional view of a hydrophilic coating and illustrates the phenomenon of capillary action acting upon microscopic voids in a hydrophilic surface, wherein a liquid droplet would be drawn into and contained.

Intermolecular forces mediate the interaction between molecules. Such forces are observable at the macroscopic level and associated with the bulk properties of material. When liquid contacts a surface, the strength of the adhesive and cohesive forces imparted on the liquid via the surface will define the shape of the liquid. As shown in FIG. 2, if adhesive forces are dominant, the liquid (1) will be pulled into the ultra-hydrophilic surface (4), whereas when cohesive forces prevail, adhesion is resisted, and the shape of the liquid is retained on the surface (as seen FIG. 1A).

Capillary action is defined as one substance's ability to draw a liquid inward. The upward and downward movement of liquid on a substrate is directly related to intermolecular forces, surface tension and contact angle, which is observable in nature. Shorebirds capture water between their upper and lower mandibles; however due to the geometry of their long beak and the opposing gravitational force, suction does not transport the droplets inward (towards the mouth). Still, by repeatably opening and closing their beak, the shorebird transfers the droplets inward toward their mouth. While surface tension plays a role in the process, the physical mechanisms responsible for the droplet transport are characterized by the spontaneous movement of a droplet on a shorebird's beak associated with hydrophilic surfaces of the beak and the contact angle of the interaction; a phenomenon coined a "capillary ratchet."

As shown in FIG. 2, the application of hydrophilic coatings across a material creates irregularities, cavities, void spaces, and patterns across the surface (6). This geometric manipulation (or hydrophilic functionalization) of the article's surface will influence the behavior and properties of the material, altering the material's structure, surface area and energy, and enhancing capillary motion. On a hydrophilic surface the contact angle (8) is less than 90-degrees (5) and results in "wetting." As the droplet is drawn inward (7, indicated by the arrow in FIG. 2.) the v-shaped cavities (6), created by the hydrophilic coating (4) function as a capillary tube. In the proposed invention, the entire article surface is coated with an ultra-hydrophilic polymer (4), creating a ubiquitous pattern of cavities (6) dispersed throughout the material that facilitates inward movement of aqueous droplets (7).

Figure 3A:
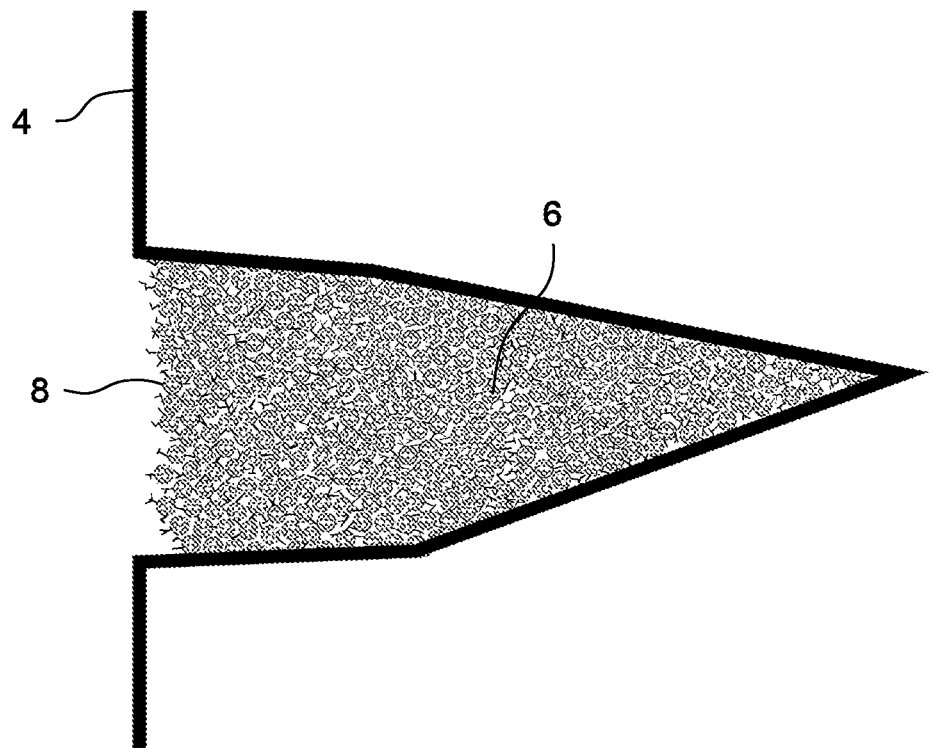
FIG. 3A and FIG. 3B represent a cross sectional view of functionalized halofullerenes application to the hydrophilic coating surface.

As shown in FIG. 3A, the application of an elastomeric hydrophilic polymer (4) at an elevated temperature (between 55.0° C.-75.0° C.) will result in spontaneous formation of cavities (6) across the article. As shown in FIG. 3A, at higher temperatures, the formed cavities (6) are relaxed, possessing a larger size or diameter compared to ambient temperatures. While temperatures are elevated and the voids regions are stretched, each cavity (6) can be imbued with a plurality of materials with antimicrobial functionalities. In the present invention, these regions are filled with an abundance of antimicrobial FD (8).

Figure 4A:
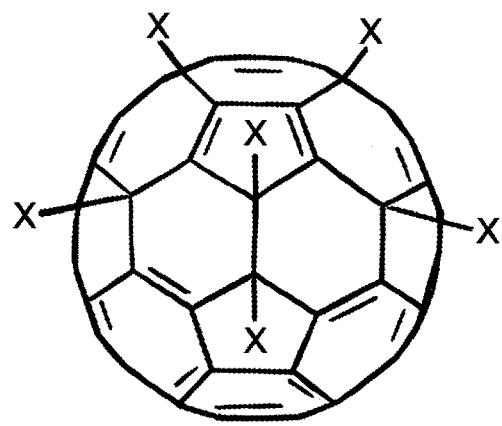
FIG. 4A, FIG. 4B, and FIG. 4C are molecular representations of an exemplary fullerene derivative (FD) of 60 carbons functionalized with 4, 8, or 24 halogens (X).
Figure 4B:
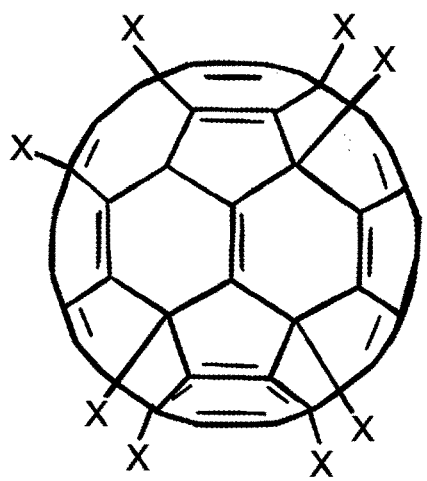
Figure 4C:
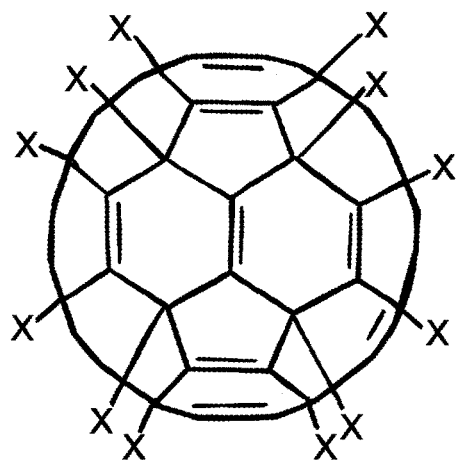

Fullerenes are capable of functionalization via numerous chemical reactions. In the present invention a halogen FD, or halofullerenes, represents a fullerene of $C_{2n}$, whereby n=10, 12, 13, 14, 15, . . . , 360, that contains multiple side-chains halogens attached to the carbon cage. As shown in FIG. 4A-C, a $C_{60}$ fullerene is functionalized with a halogen molecule. Three typical functionalization patterns for a $C_{60}$ halofullerene include: $C_{60}X_6$ (FIG. 4A), $C_{60}X_8$ (FIG. 4B), and $C_{60}X_{24}$ (FIG. 4C); whereby X=a halogen molecule (i.e.: iodine, bromine, chlorine and fluorine). The halofullerene has molecular affinity towards and attraction of pathogenic species and functionalization with highly antimicrobial halogens that caustically kill a microbe instantaneously, without losing any energy, virulence or the ability to maintain a continuous antimicrobial capability.

The use of halogenated fullerenes in the proposed invention is preferable because of the antimicrobial nature of the fullerene and halogen, as well as the incompressible properties of the fullerene. As related to this invention, the FD will occupy the void space in the coated material. At elevated temperatures the article is relaxed by the heat, creating a larger cavity region that can accept greater volumes of FD than a similar material at cool or ambient temperatures. The FD is loaded into the relaxed voids at increased temperatures and after cooling these recesses constrict, trapping the FD into the material.

Figure 3B:
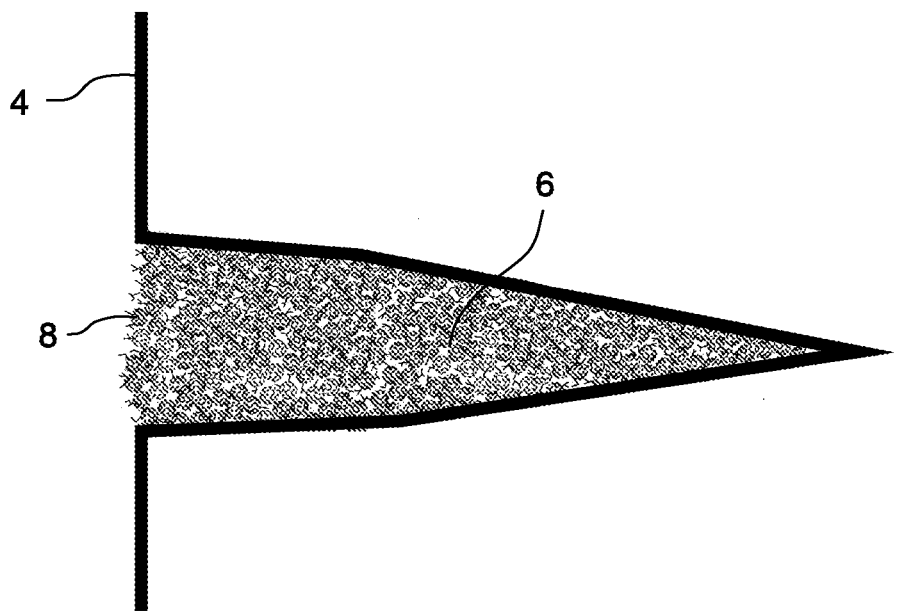

As shown in FIG. 3B, after FD (8) application the article is gradually cooled, between 0.0° C.-5.0° C., to contract the relaxed cavities (9), affixing the FD contents. The FD (8) are held in space inside the cavities (6) due to shrinkage of the cavity from slowly decreasing the ambient temperature. The FD is permanently held inside the cavity after surrounding temperatures are dropped and the material is returned to an inactive memory state. The undeformed natural material shape contracts around the FD and the projecting halogenated side chains interweave or entangle with each other, locking the FD into the void. Notably, while material constricts at cooler temperatures, the fullerenes themselves are not compressible and do not change shape or structural confirmation. The incompressible nature and large negative space of the fullerene (empty inner cage), allows for the region to accept external aqueous material via capillary action, as the packed fullerenes do not occupy space, topographically.

Upon contact with the article in this invention, microscopic void spaces or cavities (6) created by the hydrophilic coating draw the aqueous material containing pathogens inward via capillary action, the movement of water (7) is indicated by the arrow in FIG. 2. Upon capillary uptake, as shown in FIG. 3, the pathogenic material is localized to void regions (6) that are densely packed with the halogen FD (FIGS. 4A, 4B and 4C), establishing a caustic microenvironment that exerts a broad-spectrum antimicrobial effect on the adsorbs pathogenic material.

Figure 5:
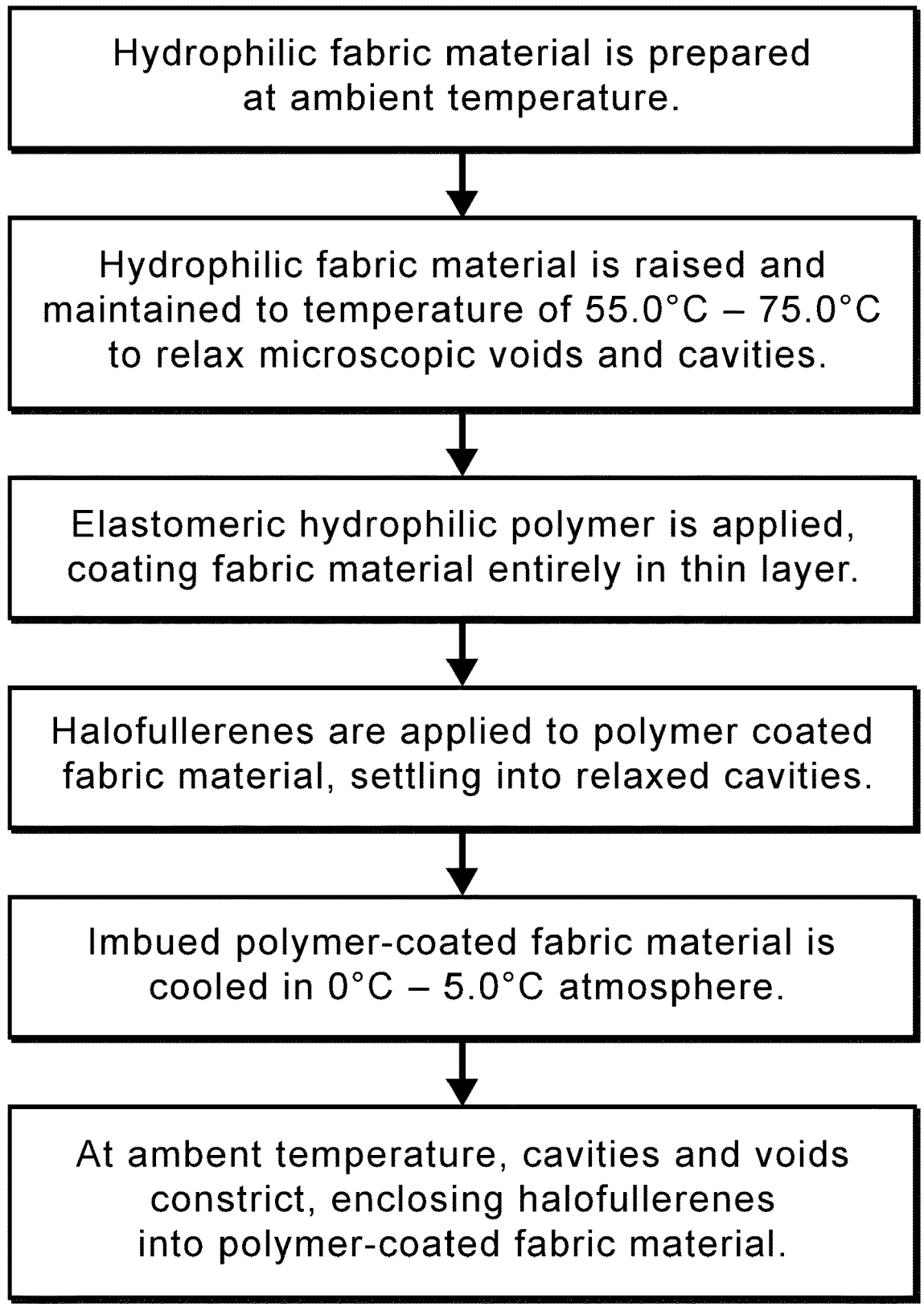
FIG. 5 is a flow-chart detailing the process of imbuing fabric material with hydrophilic coating and halofullerenes.

The method for preparing a composition comprising of an antimicrobial FD (halofullerene) is shown in FIG. 5 and includes: coating a hydrophilic fabric material with an elastomeric ultra-hydrophilic polymer at an elevated temperature (between 55.0° C.-75.0° C.); filling the relaxed cavities or void spaces of the heated elastomeric ultra-hydrophilic polymer coated article with FDs; cooling the article (between to 0.0° C.-5.0° C.); and gradually air drying and dehumidifying the coated and imbued FD containing article to room temperature.

Figure 6:
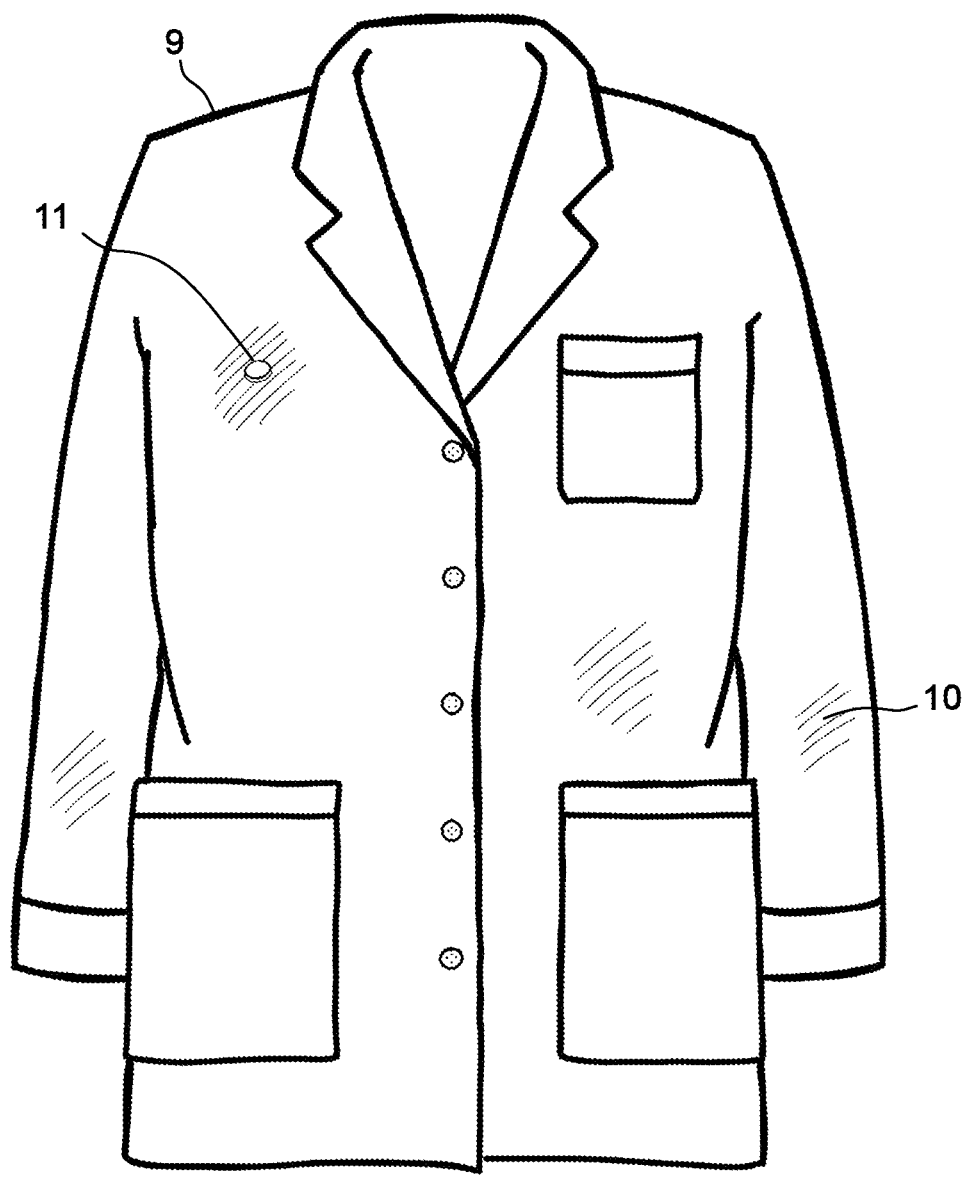
FIG. 6 illustrates a plan view of proposed quality control measures in a personal protection garment embodiment of the present invention.

A quality control technique (easy and visible) must be incorporated to verify that the fullerenes did not disassociate from the material. As such, one or multiple regions of the article (9) may be filled with magnetic endohedral fullerenes of similar size as a quality control mechanism (10), as shown in FIG. 6. The magnetic endohedral fullerene would be comprised of a ferrimagnetic material (i.e.: iron) inside of the cage or functionalized on the outer shell of the fullerene. These coated regions would enable direct end-user determination of antimicrobial FD coating by applying a small magnetic wafer or disc (11) to the region that would be held on the surface to indicate the presence of the magnetic nanomaterials in the article. The absence of magnetism in the region would convey that the FD impregnated cavities of the material were no longer filled. Additionally several magnetic endohedral fullerene doped spots can be decorated throughout the fabric.

In another embodiment, the FD coated material can be formed into an article as described above and introduced into a canister or cartridge as a bioactive, antimicrobial filter membrane. The surface of the filter article is modified with halogen functionalized FD in a process described above. Briefly, blood would flow into the antimicrobial cartridge using traditional hemodialysis methods. The blood is passed through sidewalls radially into a funnel composed of the FD modified article, before exiting through an outlet at the top of the cartridge or cannister. The antimicrobial capacity of the cartridge is linked to the high surface area of the filter membrane and FD that would be presented to the circulating blood. Specifically, free-floating pathogens would contact the caustic halogen functionalized on the cage of the fullerene resulting in pathogen destruction, mechanistically as described above. The hemofiltration cartridge, canister, column or funnel would interact with and kill circulating pathogenic material and pathogenic material associated with or bound to cellular material. The bioactive halogen FD filter would confer antimicrobial activity to pathogens in the blood, however the configuration does not function to remove, filter or separate destroyed pathogenic material. Similarly, the FDs would be retained or affixed to the membrane and not dispersed into the incoming blood or subsequently distributed systemically to the host.

In another embodiment, a saline based fluid comprised of halogen functionalized FD is used as a lavage or irrigation fluid that would exert an antimicrobial effect on pathogenic material contained in the region. The desired region of irrigation would be rinsed with the FD containing solution and then followed by a saline rinse to ensure that all particles were evacuated from the region. In a similar embodiment, a FD containing nasal spray, sinus rinse, or mouthwash could be administered by the user as an antimicrobial solution. In yet a similar embodiment, a FD salve could be applied to the external tissue regions of the mouth, nose, or other regions of the body as a bioactive barrier or used for wound healing applications. Alternatively, a FD-based mist, solution, salve, cream, or carrier would be suitable for application onto or into any region that would not result in systemic distribution of the nanomaterial in the user. Examples include a lung saline rinse rich in FD (rinse and remove), sinus cavity rinse (rinse and remove), synovial joint space rinse (rinse and remove). Encompassing the pleura, the lungs, the pericardium, the heart, the peritoneum, and the digestive organs (for treatment of bacterium like *Clostridioides difficile*). Other closed organs treatable with irrigation include the uterus, bladder and urethra. Additional applications include the eye orbital space when infections are untreatable due to the lack of circulation and lastly, as a mouth and throat gargle and rinse

The invention claimed is:

1. A textile comprising (i) a hydrophilic fabric;

and (ii) a carbon nanomaterial antimicrobial agent impregnated therein, wherein the carbon nanomaterial antimicrobial agent consists of a spherical halofullerene having the structure $C_{2n}$ whereby n=12, 13, 14, 15, . . . , 360 with halogen side chains attached to the carbon cage, wherein the carbon nanomaterial precludes proliferation of, inhibits growth of, or destroys a microorganism in biological, non-biological, or physiological fluids.

2. The textile according to claim 1, wherein the textile causes pathogen destruction is ex vivo.

3. The textile according to claim 1, further comprising a coating selected from the group consisting of polymers or copolymers of: acrylic acid (PAA), polyvinyl alcohol (PVA), polyvinyl pyrrolidone (PVP), polyethylene oxide (PEO), methacrylic acid (PMA), itaconic acid (PIA), propylene oxide and ethylene oxide [P(EO/PO)], maleic acid (PLA), 3-butene-1,2,3-tricarboxylic acid (PBA), and combinations thereof.

4. The textile according to claim 1, wherein the hydrophilic fabric is selected from the group consisting of cotton, wool, linen, silk, nylon, and blends thereof.

5. The textile according to claim 1, wherein the spherical halofullerene is a $C_{60}$ halofullerene.

6. The textile according to claim 5, wherein the spherical halofullerene has the formula $C_{60}X_6$, $C_{60}X_8$, or $C_{60}X_{24}$, wherein X is a halogen selected from iodine, bromine, chlorine, and fluorine.

7. The textile according to claim 1, which is in the form of a garment.

8. The textile according to claim 7, wherein the garment is selected from the group consisting of gowns, shirts, gloves, masks, shoe covers, and clothing.

9. The textile according to claim 1, wherein the textile is selected from the group consisting of sheets, table covers, linens, pads, drapes, towels, dressings, and bedding material.

* * * * *